(12) United States Patent
Prasad

(10) Patent No.: US 6,815,208 B2
(45) Date of Patent: Nov. 9, 2004

(54) CHEMICAL TREATMENT FOR HYDROSTATIC TEST

(75) Inventor: Rupi Prasad, Houston, TX (US)

(73) Assignee: Champion Technologies, Inc., Houston, TX (US)

( * ) Notice: Subject to any disclaimer, the term of this patent is extended or adjusted under 35 U.S.C. 154(b) by 0 days.

(21) Appl. No.: 10/293,764

(22) Filed: Nov. 13, 2002

(65) Prior Publication Data

US 2003/0148527 A1 Aug. 7, 2003

Related U.S. Application Data

(60) Provisional application No. 60/332,813, filed on Nov. 14, 2001.

(51) Int. Cl.[7] .............................................. G01N 33/18
(52) U.S. Cl. ............................ 436/39; 19/127; 19/136; 19/138; 19/174
(58) Field of Search ............................... 436/39, 8, 18, 436/19, 127, 136, 138, 183, 174, 175, 148; 252/408.1, 387

(56) References Cited

U.S. PATENT DOCUMENTS

| | | | | |
|---|---|---|---|---|
| 4,501,667 A | * | 2/1985 | Cook | 210/700 |
| 5,124,047 A | * | 6/1992 | Quach et al. | 210/699 |
| 5,183,573 A | * | 2/1993 | Kreh et al. | 210/697 |
| 5,244,600 A | * | 9/1993 | Cuisia et al. | 252/396 |
| 5,294,371 A | * | 3/1994 | Clubley et al. | 252/389.23 |
| 5,385,896 A | * | 1/1995 | Bryan et al. | 514/129 |
| 5,803,180 A | * | 9/1998 | Talley | 169/16 |
| 2003/0057401 A1 | * | 3/2003 | Craig | 252/387 |

OTHER PUBLICATIONS

Stoecker; A Practical Manual on Microbiologically Influenced Corrosion, vol. 2, Chapter 9, titled Treatment for the Mitigation of MIC, by LUTEY, 1993, 2001 by NACE International, Houston, Texas.

Borenstein, et al., Microbiologically Influenced Corrosion Failure Analysis of 304L Stainless Steel Piping System Left Stagnant After Hydrotesting with City Water, Paper No. 02446, Corrosion 2002, 2002 by NACE International, Houston, Texas.

Federal Register/ vol. 63, No. 200, Oct. 16, 1998, Final National Pollutant Discharge Elimination System , pp. 55718–55761 and Fed. Reg. vol. 66, No. 50, Mar. 14, 2001, pp. 14988–14999.

TPC Publication 3, The Role of Bacteria in the Corrosion of Oil Field Equipment, NACE, Houston, Texas, 1976, pp. 39–40.

* cited by examiner

Primary Examiner—Maureen M. Wallenhorst
(74) Attorney, Agent, or Firm—Streets & Steele; Jeffrey L. Streets

(57) ABSTRACT

A method of treating hydrotest water to inhibits oxygen corrosion, microbiologically influenced corrosion (MIC) and to allow safe discharge of water. The combination treatment plan reduces biocide usage in a high pH brine. The reduced overall chemical usage facilitates meeting environmental guidelines while also minimizing chemical cost. The method includes: adding an oxygen scavenger to remove oxygen and prevent or minimize oxygen corrosion; raising the hydrotest water pH, typically in excess of pH 9.5; adding a biocide in reduced amount; and adding a scale inhibitor to inhibit scale.

46 Claims, 2 Drawing Sheets

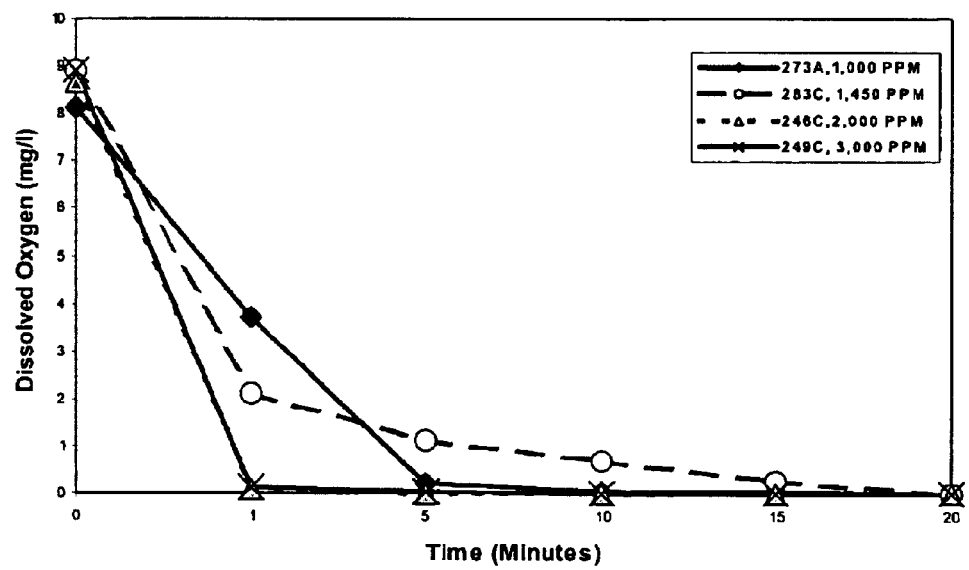
Figure 1 – Oxygen scavenging capacity of various special blends.

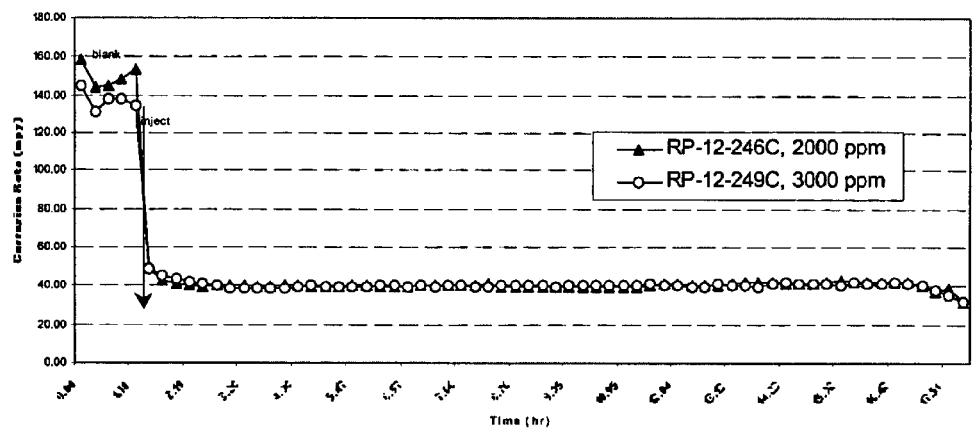
FIGURE 2 - RCE Corrosion Test. (Test condition: 120 F, 100% seawater, continuous $CO_2$ sparge.

CHEMICAL TREATMENT FOR HYDROSTATIC TEST

This application claims priority from Provisional U.S. Patent Application Ser. No. 60/332,813 filed Nov. 14, 2001.

FIELD OF THE INVENTION

The present invention relates generally to the field of chemical treatment of water used for hydrostatic tests, and, more particularly, to a method and chemistry for the reduction of oxygen and microbiologically influenced corrosion in systems requiring a hydrostatic or leak test.

BACKGROUND OF THE INVENTION

Water used for hydrostatic or leak testing is typically left in pipelines from a couple of days to years. Thus, a pipeline undergoing a hydrostatic test may become quite vulnerable to oxygen corrosion and microbiologically influenced corrosion (MIC). MIC is often established during preparational phases of plant construction or during hydrostatic testing phases, when water is first introduced into the system. Therefore, this period is critical for prevention of oxygen corrosion and MIC and therefore, the quality of the water used for hydrostatic test is of vital importance.

In relation to a hydrostatic test, the main factors that cause corrosion of steel, leading to pipeline damage, are dissolved oxygen and bacteria present in the water used for the hydrostatic test. To prevent oxygen corrosion, oxygen scavengers such as ammonium or sodium bisulfites are commonly used. Preventive measures for control of MIC include biocide treatment, pH adjustment, or sulfate ion removal.

The use of biocides has proven to be effective in controlling MIC. However, most biocides add toxicity to the treated water. The toxicity of the water creates a problem because after the completion of a hydrostatic test the water must be discharged from the tested system, often with severe environmental constraints. For example, if the water is discharged into the ocean under U.S. jurisdiction, hydrostatic test water must pass certain aquatic toxicity tests. Due to such environmental constraints, the chemical selected to treat hydrotest water must not only inhibit oxygen corrosion and MIC, but must also comply with environmental requirements when discharged.

The adjustment of pH inhibits the bacterial growth to a certain extent. Further, the mere adjustment of the pH of water does not protect pipe surfaces from oxygen corrosion, while potentially causing mineral scale problems. Thus, there remains a need for a chemical treatment regimen for water used in hydrostatic test procedures that reduces or prohibits oxygen and microbiologically influenced corrosion of ferrous metals while also meeting environmental constraints placed on the discharge of such water. The present invention is directed to solving this problem in the art.

SUMMARY OF THE INVENTION

The present invention combines a chemical treatment strategy, including biocide, oxygen scavengers, and a scale inhibitor, with an adjustment of pH. This combination chemical stratagem provides an effective option for treating hydrotest water for inhibition of oxygen corrosion, inhibition of MIC, and the safe discharge of water into the environment following the performance of a hydrostatic test.

The primary benefit of the combination treatment plan is reduced biocide usage in a high (>9.0) pH brine. The reduced overall chemical usage facilitates meeting environmental guidelines while also minimizing chemical cost. The method of the invention therefore comprises adding an oxygen scavenger to remove oxygen and prevent or minimize oxygen corrosion; raising the hydrotest water pH, typically in excess of pH 9.5 (this may be accomplished with many bases, although sodium hydroxide is typical); adding a biocide in reduced amount (the ability of the biocide to function in reduced quantity is allowed by the increase pH of hydrotest brine); and adding a scale inhibitor to inhibit scale (an increase in pH of the hydrotest brine can increase the tendency to form mineral scales, such as calcium or magnesium carbonate).

The order of the addition of the chemicals to the hydrotest water may be important, particularly if using oxygen scavengers such as bisulfite that can react with and impair the performance of many biocides. If the selected oxygen scanvenger adversely reacts with the biocide, the it is important to add oxygen scavenger prior to adding biocide and to allow adequate time for reaction.

Based on the previous scenario, a typical application would be, to first inject a package consisting of sodium hydroxide solution, oxygen scavenger, and scale inhibitor into hydrotest water. This would then be followed by injection of biocide and used for the hydrotest application. If there are no negative interactions between the selected chemicals, then all of the chemicals may be injected simultaneously or in a single package.

These and other benefits, features, and advantages of the invention will be apparent to those skilled in the art from a review of the following detailed description along with the accompanying drawings.

BRIEF DESCRIPTION OF THE DRAWINGS

FIG. 1 is a time plot of dissolved oxygen over time, illustrating the oxygen scavenging capacity of various blends, as described herein.

FIG. 2 is a time plot of a rotating cylinder electrode (RCE) corrosion test, illustrating the effectiveness of the present invention in combating corrosion.

DETAILED DESCRIPTION OF PREFERRED EMBODIMENTS

Experiments for Inhibition of Oxygen Corrosion and Scale Deposition

Many blends of NaOH solution, oxygen scavenger and scale inhibitors were made for experimentation. For the oxygen scavenger, sodium or ammonium bisulfite was used. Both the catalyzed and uncatalyzed oxygen scavengers were used. For scale inhibitors, phosphonates as well as environmentally friendly polymers were used. The stable and best performing blends were selected for final experiments.

Experiments for Inhibition of Bacterial Growth

Experiments were conducted to see if the use of biocides following the adjustment of pH could give better protection against MIC than pH adjustment alone. Various types of biocides, at various concentrations were evaluated. In the initial experiments many biocides were used. In the final experiments only two biocides were used, namely glutaraldehyde and tetrakis hydroxymethyl phosphonium sulfate (THPS). The reason for selecting these two biocides was their low toxicity profile as well as their short life in alkaline pH. For example, the half life of THPS under anaerobic condition at pH 9 is only 7 days compared to 72 days at pH 7. It should be noted that if the toxicity of discharge water is of no concern, then any biocide could be used.

Experiments to Determine the Toxicity of Chemically Treated Water

The pH of fresh water or seawater was adjusted and desired concentrations of biocides were added. The concentration of biocides in the water was measured periodically. Such monitoring provided information on the deactivation rate of biocides. To monitor the concentration of THPS and glutaraldehyde a LaMotte kit and a Glutatect kit were used, respectively. The LaMotte Company supplies the LaMotte kit. Alden Scientific manufactures the Glutatect kit. After the complete deactivation of biocide, the water was tested for aquatic toxicity. The biocides are deactivated faster in the alkaline pH. Aquatic toxicity testing showed that the deactivated products are non-toxic or have very low toxicity to aquatic organisms.

From the above three categories of experiments it was concluded that the addition of biocide at low concentrations following pH adjustment of the water inhibited bacterial growth better than pH adjustment alone. The combination treatment also worked better than high concentrations of biocide without the pH adjustment. See Example 1 below. The adjustment of hydrotest water pH with a blend containing sodium hydroxide and scale inhibitor inhibited scale formation (precipitation). See Example 2 below. The adjustment of hydrotest water pH with a blend containing sodium hydroxide, oxygen scavenger and scale inhibitor protected a metal coupon from oxygen corrosion and scale deposition. See Example 2. The residual biocides were deactivated faster in pH adjusted water, thus making the hydrotest water safe for disposal. See Example 3.

EXAMPLE 1

Cultures (in API media) of sulfate reducing bacteria (SRB) and facultative anaerobic acid producing bacteria (FAAPB) were treated separately with dilute NaOH solution to raise the pH of the culture to 9.8–10.00. The level of bacterial growth was estimated by the serial dilution method. In some experiments oxygen scavenger (ammonium bisulfite) was also included to see if it has any effect on bacterial growth. No coupons were used in these experiments.

Raised pH Combined with Biocides

In these experiments, SRB or FAAPB cultures were treated with various concentrations of biocides, after raising the pH to 9.8–10.00. The bacterial growth in the treated samples was estimated by the serial dilution method. The visual appearance of coupons in treated and untreated samples was recorded. An aldehyde and phosphonium quat were used for biocides.

Results

The results of time kill studies using SRB cultures treated with NaOH are shown in Table 1. Raising the pH to 9–10 inhibited bacterial growth compared to the control. However, a total kill was not observed. The addition of ammonium bisulfite (combined with high pH) significantly reduced the bacterial growth (Table 2). When ammonium bisulfite and glutaraldehyde, were added in combination, there was a 100% bacterial kill after 5 hours contact (Table 2). Black patches were observed on coupons inserted in the raised pH medium, suggesting the growth of sessile bacteria.

The treatment with raised pH in combination with biocides was very effective (Table 3). It was also noted that less biocide was needed for the total kill. The coupons placed in most of the combination treatment bottles remained clean indicating the absence of sessile bacteria.

TABLE 1

Effect of pH on SRB Population

| | Log of SRB/mL | | | | | |
|---|---|---|---|---|---|---|
| | Experiment 1 (20 days) | | Experiment 2 (10 Days) | | Experiment 3 (10 Days) | |
| Treatment | #1 Bottle | #2 Bottle | #1 Bottle | #2 Bottle | #1 Bottle | #2 Bottle |
| 0 hrs. control | ≧6 | ≧6 | ≧6 | ≧6 | 5 | 5 |
| 0 hrs. pH | ≧6 | ≧6 | ≧6 | ≧6 | 5 | 4 |
| 5 hrs. control | ≧6 | ≧6 | ≧6 | ≧6 | 4 | 5 |
| 5 hrs. pH | 2 | 3 | 3 | 3 | 3 | 4 |

TABLE 2

Effect of pH, Ammonium Bisulfite and Glutaraldehyde on SRB Population

| | Log of SRB Cells/mL | |
|---|---|---|
| Treatment | Experiment 1 (7 Days) | Experiment 2 (7 Days) |
| 0 hr. Control | ≧6 | ≧6 |
| 0 hr. pH | ≧6 | ≧6 |
| 5 hrs. Control | ≧6 | ≧6 |
| 5 hrs. pH | 4 | 4 |
| NH$_4$HSO$_3$ (200 PPM) | 2 | 2 |
| NH$_4$HSO$_3$ + Glutaraldehyde | 0 | 0 |

TABLE 3

Evaluation of Biocides in pH Adjusted Medium Containing Sulfate Reducing Bacteria (SRB)

| Treatment | Concentration | Log of Bacterial Cells/ml | Observation of Coupon |
|---|---|---|---|
| Control | 0 | 4–6 | Heavy black deposit |
| pH 10 | 0 | 1–3 | Patches to a heavy black deposit |
| Glutaraldehyde | 150 | 0 | Clean |
| Glutaraldehyde | 75 | 0 | Clean |
| Glutaraldehyde | 25 | 0–1 | Small black spots observed |
| Glutaraldehyde | 12.5 | 0 | Black patches |
| THPS | 112.5 | 0 | Clean |
| THPS | 37.5 | 0–1 | Few black spots |
| THPS | 18.75 | 0–3 | Black patches |
| pH 10 + Glutaraldehyde | 25 | 0 | Clean |
| pH 10 + Glutaraldehyde | 12.5 | 0–1 | Clean |
| pH 10 + THPS | 37.5 | 0 | Clean |
| pH 10 + THPS | 12.5 | 1–3 | Patches of heavy deposits |

From the results it is evident that the adjustment of pH alone does not inhibit bacterial growth completely. It is also evident that significantly less biocide is needed to completely inhibit the bacterial growth in pH adjusted medium. The absence of black iron precipitate on coupons further suggests that sessile bacterial growth is also inhibited at low biocide concentrations in pH-adjusted medium. These results lead to the conclusion that as low as 10–12 PPM of 50% glutaraldehyde is sufficient to inhibit planktonic as well as sessile bacterial growths in water with pH adjusted to 10 (FIG. 5).

EXAMPLE 2

More than thirty special blends containing NaOH, oxygen scavenger and scale inhibitor were made. Time kill studies were conducted to evaluate the effect of these special blends on bacterial growth. For the time kill studies cultures of SRB and anaerobic bacteria as well as filtered Galveston seawater were used. Galveston seawater was filtered through 50 μm filter. The time kill studies were basically the same as in the raised pH studies described earlier. The only difference was that in these studies, the pH was raised by the special blends and natural seawater was included in addition to bacterial cultures. Usually, 1,500 to 3,000 PPM of the special blends were used to raise the pH to 9.6–9.8. In some experiments, the seawater was treated only with NaOH or oxygen scavenger for comparison purposes. A piece of mild carbon steel coupon (1"×0.3") was inserted into the treated water to monitor MIC and corrosion in all of the experiments.

The bacterial growth was monitored for 20 days. The monitoring of coupons in the treated samples continued for weeks to months. The products that inhibited the bacterial growth and kept the coupons clean were selected. These selected products were re-evaluated using the bacterial cultures and the filtered seawater.

Results

Most of the special blends were effective in controlling bacterial growth. The results shown in Table 5 are typical. The treatment of bacterial cultures with special blends inhibited the bacterial growth but did not give a 100% kill. However, when a biocide was used in combination with a special blend, a 100% kill was observed. Furthermore, a lower concentration of biocide was required for a 100% kill when used in combination with a special blend. Similar results were when Galveston seawater was treated with the special blends (Table 6). It is clear from these results that less biocide is needed to kill bacterial cells when used in combination with raised pH than when used alone.

No scale precipitate was observed in seawater treated with the special blends. The appearance of coupons inserted in treated seawater varied. A brownish to blackish precipitate occurred overnight covering the coupon surface in untreated seawater in seawater treated with NaOH solution only, a brownish to blackish precipitate also occurred overnight. However, after a few weeks, patches of deposits were observed on the coupons. Coupons in seawater treated with oxygen scavenger alone turned black after two weeks following the treatment. In general, coupons in seawater treated with the special blends stayed clean for a longer time (more than three weeks). However, after a month or so, black patches started to develop on coupons placed in some of the treated seawater. The analysis of the deposits indicated chemical deposit as well as bacterial cells. These results indicated that although the special blends were able to control planktonic bacterial growth, some of these special blends were unable to protect the coupons from sessile bacterial growth. Out of more than 30 special blends, three blends were selected—283C, 246C and 249C. These three blends inhibited bacterial growth and protected the coupons for over a month. However, after 3 months black patches developed on the coupons in seawater treated with 283C. Therefore, 283C was eliminated from further experiments.

TABLE 4

The Weight Percent Composition of Selected Blends

| | 246C | 249C | 283C |
|---|---|---|---|
| Water | 64.00 | 60.00 | 64.00 |
| 50% NaOH | 20.00 | 20.00 | 20.00 |
| Scale Inhibitor | 1.00 | 5.00 | 5.00 |
| Oxygen Scavenger | 15.00 | 15.00 | 11.00 |

TABLE 5

Effect of Special Blends on
Anaerobic and SRB Growth in Culture

| | | Log of Bacterial Cells/ml | |
|---|---|---|---|
| Chemical | PPM (pH) | SRB | Anaerobic |
| Control | 0 (~7) | 5–6 | 5–6 |
| 50% Glutaraldehyde | 50 (~7) | 0–1 | ≧3 |
| 35% THPS | 50 (~7) | 0–1 | ≧3 |
| 111C | to pH 9.7 | ≧3 | 1–2 |
| 111C + 50% Glutaraldehyde | 25 (9.7) | 0 | 2 |
| 111C + 35% THPS | 25 (9.7) | 2 | 2 |
| 283C | to pH 9.7 | 0 | 2 |
| 283C + 50% Glutaraldehyde | 25 (9.7) | 0 | 0–1 |
| 283C + 50% Glutaraldehyde | 12.5 (9.7) | 0 | 0–1 |
| 283C + 35% THPS | 25 (9.7) | 0 | 0–1 |
| 283C + 35% THPS | 12.5 (9.7) | 0 | 0–1 |
| 249C | to pH 9.7 | 0–1 | 2 |
| 249C + 50% Glutaraldehyde | 25 (9.7) | 0 | 0–1 |
| 249C 35% THPS | 25 (9.7) | 0 | 1 |
| 246C | to pH 9.7 | 0–1 | 2 |
| 246C + 50% Glutaraldehyde | 25 (9.7) | 0 | 0–1 |
| 246C + 35% THPS | 25 (9.7) | 0 | 0–1 |

TABLE 6

Effect of Special Blends on SRB Growth in Natural Seawater

| Chemical | PPM (pH) | Log of Bacterial Cells/ml |
|---|---|---|
| Control | 0 | 3 |
| 50% Glutaraldehyde | 25 | 1 |
| 35% THPS | 25 | 1 |
| 283B | to pH 9.8 | 1–2 |
| 283C | to pH 9.8 | 1–2 |
| 283B + 50% Glutaraldehyde | 12.5 (9.8) | 0–1 |
| 283C + 50% Glutaraldehyde | 12.5 (9.8) | 0–1 |

Oxygen Measurement

To be sure that the special blends scavenge oxygen, experiments were conducted to measure the oxygen level following the addition of chemicals. For this procedure standard BOD bottles were used. The bottles were filled with 300 ml of seawater and the concentration of dissolved oxygen (DO) was determined with an oxygen meter (WTW-OXI197-S). Then a desired concentration of the special blend was added and the DO content was monitored for 15–20 minutes. At the end of this period a residual sulfite level in the treated water sample was determined using Hach method 8071. The final pH of the treated water was also determined.

A typical example of oxygen scavenging capacity of the special blends is shown in FIG. 1. Most of the blends scavenged all of the DO within 15–20 minutes. The final pH range of the treated seawater was between 9.5 and 9.8. The sulfite residuals in the treated water varied from 4 to 90 PPM.

Corrosion Test

A rotating cylinder electrode (RCE) Corrosion Test was conducted to see if the selected products, 249C and 246C, were corrosive at 3000 and 2000 PPM. Galveston seawater was used as a blank. The corrosion rate was measured and data were analyzed. The RCE test was conducted under a $CO_2$ sparge. Experiments were also conducted to measure the corrosion rate by weight loss. For these experiments, seawater was treated with 249C and 246C at 3,000 and 2,000 PPM respectively. Pre-weighed mild steel coupons (½"×3"× 1/16" w/9/32" hole) were placed in each of the bottles containing treated water. The bottles were placed in the dark for 3–4 weeks at room temperature. At the end of this period, the coupons were cleaned and weighed. The corrosion rate was calculated from the weight difference.

The results of the RCE tests are shown in Table 7 and FIG. 2. The blank corrosion rate was >100 mils per year (MPY). The addition of special blends, 246 C and 249 C, significantly reduced the corrosion rate. This suggested that these specials blends are not corrosive and may give some corrosion protection. The data obtained by the weight loss method are shown in Table 8. The results confirmed the results of the RCE tests. The experimental data suggest the special blends are capable of inhibiting oxygen corrosion and MIC when used in combination with low doses of biocides.

TABLE 7

RCE Test Results of Treated Seawater

| Chemicals | Dose, PPM | Blank CR (MPY) | Integrated Inhibited CR (MPY) | % Protection | Mass Loss (MG) |
|---|---|---|---|---|---|
| 246 C | 2000 | 149.9 | 39.76 | 73.48 | 5.5 |
| 249 C | 3000 | 137.46 | 39.56 | 71.22 | 5 |

TABLE 8

Corrosion Measurement by Weight Loss Method
(Coupons immersed in treated seawater for 20 days)

| Chemicals | Concentration (PPM) | MPY Calculated |
|---|---|---|
| Control | 0 | 0.38 |
| 246C | 2,000 | 0.31 |
| 249C | 3,000 | 0 |

EXAMPLE 3

Galveston seawater was treated with NaOH solution and with blends of NaOH and chemicals separately to raise the pH to 9–10.25. 12–100 PPM of 50% glutaraldehyde was added to each aliquot of pH-adjusted water. The treated water was left at room temperature. The concentration of glutaraldehyde was monitored for 9–20 days, using Glutatect kit. In another experiment, 100 PPM of 75% THPS was added to Galveston seawater following pH adjustment with NaOH. THPS concentration was monitored using a LaMotte Kit. Data are shown in Table 9.

TABLE 9

Deactivation of Biocides in Galveston
Sea Water (pH adjusted to 10) PPM Biocide.

| Treatment | PPM at 0 Hr | 2 Days | PPM after 9 Days |
|---|---|---|---|
| Sea Water + 100 PPM glutaraldehyde | ~40 | 20–40 | 20–40 |
| Sea Water pH 10 + 100 PPM glutaraldehyde | ~40 | 20–40 | 10–20 |
| Sea Water + 100 PPM THPS | 132 | 104 | 68 |

TABLE 9-continued

Deactivation of Biocides in Galveston
Sea Water (pH adjusted to 10) PPM Biocide.

| Treatment | PPM at 0 Hr | 2 Days | PPM after 9 Days |
|---|---|---|---|
| Sea Water, pH + 100 PPM THPS | 136 | 58 | 14 |

The glutaraldeyde residual in seawater treated with special blends is shown in Table 10. The THPS residual could not be determined due to the interference of sulfite. After 5–10 days, the biocide residual was below 5 PPM. This is exactly what was desired. Glutaraldehyde is more effective in neutral to slightly alkaline medium and gets deactivated at higher pH. So, by treating the seawater with a special blend, the bacterial population was reduced, oxygen was scavenged and the pH was raised to >9. When a biocide was added, it killed the remaining bacteria and the biocide residual was deactivated in the alkaline pH. The end result is that the treated water is non-toxic or substantially less toxic when compared to seawater treated with 150–200 PPM of biocide.

TABLE 10

Glutaraldehyde Residual in Seawater Treated With
Special Blends and 12.5 PPM of Glutaraldehyde

| | PPM Glutaraldehyde | | | |
|---|---|---|---|---|
| Chemical | Day 1 | Day 2 | Day 10 | Day 15 |
| Control* | 10 | 10 | 5–10 | 5–10 |
| 161A | 10 | 5–10 | 5 | 2–5 |
| 161B | 10 | 5–10 | 5 | 2–5 |

*Control contained seawater + 12.5 PPM of Glutaraldehyde.

Toxicity

Three of the most promising special blends were tested 249C, 246C, and 283C. Galveston seawater was treated separately with 249C, 246C and 283C at 3,000 PPM, 2,000 PPM and 1,450 PPM respectively. The treated water was then subjected to a static renewal toxicity test (using Mysid and Menidid species). The EPA requires this toxicity test for water discharged into the Gulf of Mexico.

The results of the static renewal toxicity tests are shown in Table 11. Water treated with 283C was the least toxic. The toxicity of 246C and 249C treated water was higher than expected, although better than that treated with a biocide alone. The toxicity of seawater treated with ammonium bisulfite and biocides was also high. The results indicate that sea water treated with a special blend in combination with low doses of biocides can meet the environmental constraints for safe discharge. Such treatment will be more cost effective because no neutralization is required prior to discharge.

TABLE 11

Toxicity of Seawater with a Special Blend and Biocides

| | NOEC/LOEC % | |
|---|---|---|
| Special Blend (Concentration) | M. Beryllina | M. Bahia |
| 283C (1450 PPM) | 100/>100 | 50/100 |
| 283C (1,450 PPM) + 25 PPM Glutaraldehyde | 50/100 | 50/100 |
| 283C (1450 PPM) + 37.5 PPM THPS | 100/>100 | 50/100 |
| 249C (3,000 PPM) | 6.5/12.5 | 25/50 |
| 246C (2,000 PPM) | 12.5/25 | 25/50 |
| 150 PPM Ammonium Bisulfite + 150 PPM THPS | <9.6/9.6 | <9.6/9.6 |
| 150 PPM Ammonium Bisulfite + 125 PPM Glutaraldehyde | 12.0/24.6 | <9.6/9.6 |
| 150 PPM of THPS | 12.0/24.6 | <9.6/9.6 |

* NOEC = No Observed Effect Concentration
* LOEC = Lowest Observed Effect Concentration Conclusion Our experimental data showed that bacterial growth is inhibited by raising the pH to >9.0. 100% bacterial kill is achieved with a reduced amount of biocide when used in combination with the pH-adjusted water. The results also show that special blends can be made that raise the pH of seawater, scavenge the oxygen and protect mild steel coupons from corrosion and MIC. The toxicity of the water treated with the special blend in combination with a low concentration of biocide was much lower than the toxicity of water treated with biocide alone at high concentration. In brief, our data indicate that a combination treatment plan for hydrotest water can meet all the requirements. It gives corrosion and MIC protection, complies with environmental regulations for safe water discharge, and minimizes chemical cost.

I claim:

1. A method of performing a hydrostatic test of a closed system, comprising the steps of:
   a. adding a base, oxygen scavenger, and scale inhibitor into a quantity of hydrostatic test water; and then
   b. adding an effective quantity of a biocide into the hydrostatic test water to inhibit microbiologically influenced corrosion; and
   c) using the water to perform a hydrostatic test of a closed system.

2. The method of claim 1, further comprising the step of discharging the hydrostatic test water from the closed system into the environment after the hydrostatic test.

3. The method of claim 2, wherein the hydrostatic test water discharged to the environment has a toxicity below a predetermined limit.

4. The method of claim 2, further comprising:
   deactivating the biocide at a pH greater than 9 prior to discharging the water.

5. The method of claim 2, further comprising:
   deactivating at least half of the biocide before discharging any of the hydrostatic test water from the closed system to the environment.

6. The method of claim 2, further comprising:
   deactivating at a least a portion of the biocide at a pH greater than 9.5.

7. The method of claim 6, wherein no other neutralization is required prior to discharge.

8. The method of claim 1, wherein the biocide is selected from the group consisting of glutaraldehyde and tetrakis hydroxymethyl phosphonium sulfate.

9. The method of claim 1, wherein the base is sodium hydroxide, the oxygen scavenger is ammonium bisulfite, and the biocide is glutaraldehyde.

10. The method of claim 1, wherein the biocide is provided at a concentration between 12.5 and 37.5 ppm.

11. The method of claim 1, wherein the biocide is provided at a concentration between 12.5 and 25 ppm.

12. The method of claim 1, wherein the base, oxygen scavenger and scale inhibitor are added as a package comprising between 60 and 64 wt. % water, about 20 wt. % sodium hydroxide, between 1 and 5 wt. % scale inhibitor, and between 11 and 15 wt. % oxygen scavenger.

13. The method of claim 1, wherein the oxygen scavenger is selected from the group consisting of sodium bisulfite, ammonium bisulfite, and combinations thereof.

14. The method of claim 1, wherein the base is sodium hydroxide.

15. The method of claim 1, wherein the scale inhibitor is a phosphonate.

16. The method of claim 1, wherein the biocide has a half life of 7 days or less at the pH of the hydrostatic test water.

17. The method of claim 1, further comprising:
allowing adequate time for the oxygen scavenger to react with dissolved oxygen in the hydrostatic test water.

18. The method of claim 17, wherein the oxygen scavenger will adversely react with the biocide when mixed.

19. The method of claim 1, characterized in that the method inhibits oxygen corrosion and microbiologically influenced corrosion in the hydrostatic test.

20. The method of claim 1, further comprising:
adding a sufficient amount of a scale inhibitor to offset the increased tendency to form scale at an increased pH in hydrostatic test water.

21. A method of treating hydrostatic test water, comprising the steps of:
a. adding a quantity of a base sufficient to raise the pH of the test water to greater than 9; and then
b. adding a biocide to the test water.

22. The method of claim 21, wherein the biocide is selected from the group consisting of glutaraldehyde and tetrakis hydroxymethyl phosphonium sulfate.

23. The method of claim 21 further comprising:
adding an oxygen scavenger and scale inhibitor to the test water along with the base prior to adding the biocide.

24. The method of claim 23, wherein the oxygen scavenger is ammonium bisulfite, and the biocide is glutaraldehyde.

25. The method of claim 23, wherein the base, oxygen scavenger and scale inhibitor are added as a package comprising between 60 and 64 wt. % water, about 20 wt. % sodium hydroxide, between 1 and 5 wt. % scale inhibitor, and between 11 and 15 wt. % oxygen scavenger.

26. The method of claim 23, wherein the oxygen scavenger is selected from the group consisting of sodium bisulfite, ammonium bisulfite, and combinations thereof.

27. The method of claim 23, wherein the scale inhibitor is a phosphonate.

28. The method of claim 23, further comprising:
allowing adequate time for the oxygen scavenger to react with dissolved oxygen in the test water.

29. The method of claim 28, wherein the oxygen scavenger will adversely react with the biocide when mixed.

30. The method of claim 23, characterized in that the method inhibits oxygen corrosion and microbiologically influenced corrosion.

31. The method of claim 23, further comprising using the water to perform a hydrostatic test of a closed system; discharging the water from the closed system into the environment; and deactivating at least half of the biocide before discharging any of the hydrostatic test water from the closed system to the environment.

32. The method of claim 31, wherein no other neutralization is required prior to discharge.

33. The method of claim 21, wherein the biocide is selected from the group consisting of glutaraldehyde, THPS, and combinations thereof.

34. The method of claim 33, wherein the biocide is provided at a concentration between 12.5 and 37.5 ppm.

35. The method of claim 33, wherein the biocide is provided at a concentration between 12.5 and 25 ppm.

36. The method of claim 21, wherein the base is sodium hydroxide.

37. The method of claim 21, further comprising:
deactivating the biocide after step b.

38. The method of claim 21, wherein the biocide has a half life of 7 days or less at the pH of the hydrostatic test water.

39. The method of claim 21, further comprising:
deactivating at a least a portion of the biocide after step b.

40. The method of claim 21, further comprising:
adding a sufficient amount of a scale inhibitor to offset the increased tendency to form scale at the an increased pH.

41. A method of treating hydrostatic test water, comprising the steps of:
raising the pH of the hydrostatic test water to greater than 9;
scavenging oxygen from the hydrostatic test water with a chemical oxygen scavenger; and
after scavenging oxygen, adding an effective quantity of a biocide into the hydrostatic test water to inhibit microbiologically influenced corrosion, wherein the biocide and the chemical oxygen scavenger are reactive.

42. The method of claim 41, further comprising: deactivating at a least a portion of the biocide at the pH greater than 9.

43. The method of claim 42, further comprising the steps of using the water to perform a hydrostatic test of a closed system; and
discharging the hydrostatic test water having the deactivated biocide from the closed system into the environment after the hydrostatic test.

44. The method of claim 41, wherein the biocide is selected from the group consisting of glutaraldehyde and tetrakis hydroxymethyl phosphonium sulfate.

45. The method of claim 44, wherein the oxygen scavenger is selected from the group consisting of sodium bisulfite, ammonium bisulfite, and combinations thereof.

46. The method of claim 41, further comprising:
allowing adequate time for the oxygen scavenger to react with the oxygen before adding the biocide.

\* \* \* \* \*